United States Patent [19]

Le Hen-Ferrenbach et al.

[11] Patent Number: 5,714,154
[45] Date of Patent: Feb. 3, 1998

[54] PROCESS FOR THE PRODUCTION OF MULTIPLE W/O/W EMULSIONS

[75] Inventors: Catherine Le Hen-Ferrenbach, Meaux; Isabelle Terrisse, Toulouse; Armelle Magnet, Paris; Monique Seiller, Sceaux; Francis Puisieux, Maisons-Alfort; Jean-Louis Grossiord, St. Germain les Corbeil, all of France

[73] Assignee: Henkel Kommanditgesellschaft auf Aktien, Duesseldorf, Germany

[21] Appl. No.: 532,836

[22] PCT Filed: Mar. 30, 1994

[86] PCT No.: PCT/EP94/00996

§ 371 Date: Dec. 20, 1995

§ 102(e) Date: Dec. 20, 1995

[87] PCT Pub. No.: WO94/22414

PCT Pub. Date: Oct. 13, 1994

[30] Foreign Application Priority Data

Apr. 7, 1993 [DE] Germany .................. 43 11 445.8

[51] Int. Cl.$^6$ .................................. A61K 9/113
[52] U.S. Cl. .................. 424/401; 424/484; 424/486
[58] Field of Search .......................... 424/401, 484, 424/486

[56] References Cited

FOREIGN PATENT DOCUMENTS

| | | |
|---|---|---|
| 0042827 | 12/1981 | European Pat. Off. . |
| 4010393 | 10/1991 | Germany . |
| 4039950 | 6/1992 | Germany . |
| 4103489 | 8/1992 | Germany . |
| 4122033 | 1/1993 | Germany . |
| 5715829 | 1/1982 | Japan . |
| 7015829 | 1/1982 | Japan . |
| 00166604 | 8/1985 | Japan . |
| 9218227 | 10/1992 | WIPO . |

OTHER PUBLICATIONS

De Luca, et al., "A Stable w/o/w Multiple Emulsion", Cosmetics & Toiletries, vol. 105, Nov., 1990, pp. 65,66 and 69 only.

Matsumoto, et al., "An Attempt at Preparing Water–in–Oil–in–Water Multiple–Phase Emulsions", Journal of Colloid and Interface Science, vol. 57, No. 2, Nov., 1976, pp. 353–361.

Lin, et al., "Physical Parameters and Release Behaviors of W/O/W Multiple Emulsions Containing Cosurfactants and Different Specific Gravity of Oils", Pharm. Acta. Helv., 66, Nr. 12 (1991), pp. 342–347.

Dupinay, et al., "Mise en Gelule et Liberation D'un Principe Actif en Milieu Pateux", Bull. Tech./Gattefosse, Reg. 80, 27–31 (1987).

DeLuca, et al., "Les emulsions mutiples", International Journal of Cosmetic Science, 13, (1991), pp. 1–21.

Zhang, et al., "Preparation of Stable W/O/W Type Multiple Emulsion Containing Water–Soluble Drugs and in Vitro Evaluation of Its Drug–Releasing Properties", Yakugaku Zasshi 112 (1) (1992) pp. 73–80.

Law, et al., "Stabilisation of W/O/W Multiple Emulsions By Interfacial Complexation of Macromolecules and Nonionic Surfactants", Journal of Controlled Release, 3 (1986) pp. 279–290.

R. Perron et C. Paquot, "Preparation des ethers–oxydes symetriques derives des alcools aliphatiques satures a longue chaine", Bull Soc. Chim. France, No. 72, pp. 333–337.

ROEMPP Chemie Lexikon, vol. 5, 1992, pp. 4302–4303.

DeLuca et al. "A Stable W/O/W Multiple Emulsion", Cosmetics & Toiletries, vol. 105, pp. 65–66 (1990).

Henkel KGA (Oct.–1991), translation of WO 9115184.

*Primary Examiner*—Jeffrey C. Mullis
*Attorney, Agent, or Firm*—Wayne C. Jaeschke; John E. Drach; Henry E. Millson, Jr.

[57] ABSTRACT

A process for the production of multiple w/o/w emulsions in which a) a mixture of an oil and a lipophilic emulsifier I comprising glycerol and/or oligoglycerol or polyglycerol fatty acid esters is initially processed with intensive shearing to form a w/o pre-emulsion A, and b) the w/o pre-emulsion A is then further treated with an aqueous emulsifier II comprising adducts of ethylene oxide with fatty alcohols and/or sterols and, optionally, fatty alcohols, wherein the treatment is accompanied by gentle shearing;

and to the resulting multiple w/o/w emulsions and their use in the preparation of cosmetic and pharmaceutical products.

18 Claims, No Drawings

PROCESS FOR THE PRODUCTION OF MULTIPLE W/O/W EMULSIONS

BACKGROUND OF THE INVENTION

1. Field of the Invention

This invention relates to a process for the production of multiple w/o/w emulsions in which a w/o pre-emulsion is initially prepared with intensive shearing from water, an oil and an emulsifier I and the w/o pre-emulsion thus formed is subsequently treated with an aqueous emulsifier II with gentle shearing, to multiple w/o/w emulsions obtainable by this process and to the use of these multiple w/o/w emulsions for the production of cosmetic and pharmaceutical products.

2. Statement of Related Art

Multiple emulsions are emulsions of emulsions. Depending on their production process, they are either multiple water/oil/water (w/o/w) or oil/water/oil (o/w/o) emulsions. The most important application of multiple emulsions lies in the processing of active substances, which would otherwise be immiscible with one another, in a single formulation. Another advantage is that the active substances can be released under control over a prolonged period. Accordingly, multiple emulsions are of particular significance for the production of cosmetic and pharmaceutical products [Cosm. Toil. 105, 65 (1990)].

A particularly suitable process for the production of multiple emulsions is described by S. Matsumoto in J. Coll. Interf. Sci. 57, 353 (1976). In this process, a pre-emulsion is initially prepared with intensive shearing at elevated temperature and is subsequently introduced into an aqueous solution of a hydrophilic emulsifier with gentle shearing at ambient temperature. Sorbitan monooleate and a polyethylene glycol derivative are used as the pair of emulsifiers.

In addition, it is known from the extensive prior art that, basically, monoglycerides, sorbitan esters, polysorbates and highly ethoxylated fatty alcohols may be used as hydrophilic emulsifiers for the production of multiple emulsions, cf. the articles in Pharm. Acta. Helv. 66, 343 (1991), and by Seiller and Luca in Bull. Tech./Gattefosse Rep. 80, 27 (1987), S. T. P. Pharma 4, 679 (1988) and Int. J. Cosmet. Sci. 13, 1 (1991).

In addition, w/o/w emulsions containing glycerol trifatty acid esters as oil component and hydrophilic polymers, such as gelatine for example, as stabilizer are known from Yakugaku Zasshi 112, 73 (1992). The use of albumin and polyacrylates as stabilizers for the water phase and nonionic surfactants for the oil phase is known from J. Controlled Release 3, 279 (1986). Unfortunately, formulations such as these have proved to be inadequately stable in storage, particularly in the event of variations in temperature.

Accordingly, a particular problem in the production of multiple emulsions lies in the choice of suitable pairs of emulsifiers which provide for adequate thermal stability, even in the event of prolonged storage. Another disadvantage is that mineral oils showing unfavorable biodegradability are normally used as the oil component.

Accordingly, the problem addressed by the present invention was to provide a new process for the production of multiple w/o/w emulsions which would be free from the disadvantages mentioned above.

DESCRIPTION OF THE INVENTION

The present invention relates to a process for the production of multiple w/o/w emulsions, in which a) a mixture of an oil and a lipophilic emulsifier I from the group of glycerol and/or oligoglycerol or polyglycerol fatty acid esters is initially processed with intensive shearing to form a w/o pre-emulsion A and b) the w/o pre-emulsion A is then further treated with an aqueous emulsifier II from the group of adducts of ethylene oxide with fatty alcohols and/or sterols and, optionally, fatty alcohols, the treatment being accompanied by gentle shearing.

It has surprisingly been found that the multiple w/o/w emulsions obtainable by the process according to the invention remain stable in storage for long periods, even in the event of significant variations in temperature. The invention includes the observation that multiple emulsions with distinctly improved biodegradability in relation to the prior art can be made available through the choice of the oils mentioned and the absence of polymeric stabilizers.

Oils

Suitable oils for the production of the multiple w/o/w emulsions according to the invention are dialkyl cyclohexanes and dialkyl ethers.

The dialkyl cyclohexanes are known substances which may be obtained by the relevant methods of preparative organic chemistry. One process for their production, for example, comprises subjecting aromatic dialkyl compounds (ortho-, meta-, para-xylene) from the BTX fraction of petroleum to catalytic hydrogenation.

The dialkyl cyclohexanes suitable for use in accordance with the invention correspond to formula (I):

$$R^1-C-R^2 \qquad (I)$$

in which $R^1$ and $R^2$ independently of one another represent alkyl radicals containing 1 to 12 carbon atoms and C is a cyclohexyl radical. Typical examples are dimethyl cyclohexane, diethyl cyclohexane, methylethyl cyclohexane, dipropyl cyclohexane, di-n-butyl cyclohexane, ditert.butyl cyclohexane, di-2-ethylhexyl cyclohexane and, in particular, di-n-octyl cyclohexane.

Dialkyl ethers are compounds corresponding to formula (II):

$$R^3-O-R^4 \qquad (II)$$

in which $R^3$ and $R^4$ independently of one another represent alkyl radicals containing 6 to 22 carbon atoms.

Dialkyl ethers are also known substances which may be obtained by the relevant methods of preparative organic chemistry. Processes for their production, for example by condensation of fatty alcohols in the presence of p-toluenesulfonic acid, are known for example from Bull. Soc. Chim. France, 333 (1949), DE-A1 40 39 950 (Hoechst) and DE-A1 41 03 489 (Henkel). Symmetrical dialkyl ethers containing 6 to 12 carbon atoms in the alkyl radicals are preferred from the applicational point of view. Dialkyl ethers of formula (II), in which $R^3$ and $R^4$ represent octyl and/or 2-ethylhexyl radicals, show particularly rapid emulsifying power. Accordingly, the particularly preferred dialkyl ethers according to the invention are di-n-octylether and di-2-ethylhexyl ether.

The oils may be used in quantities of 10 to 30% by weight and preferably 15 to 25% by weight, based on the pre-emulsion A.

Emulsifier I

Glycerol and/or oligoglycerol or polyglycerol esters may be used as the emulsifier I. Typical examples are technical monoesters and/or diesters of glycerol with fatty acids containing 12 to 22 carbon atoms, such as for example glycerol monolaurate, glycerol monopalmitate, glycerol monostearate, glycerol monoisostearate, glycerol monooleate and glycerol monobehenate. Other typical examples are monoesters and/or diesters of oligoglycerol or polyglycerol mixtures (degree of self-condensation 2 to 20 and preferably 2 to 10) of the above-mentioned fatty acids containing 12 to 22 carbon atoms, such as for example polyglycerol diisostearate or polyglycerol dioleate. It has proved to be of particular advantage to use mixtures of glycerol and oligoglycerol or polyglycerol esters, for example consisting of glycerol monooleate and triglycerol diisostearate (mixing ratio 80:20 parts by weight for example). The emulsifiers I may be used in quantities of 1 to 10% by weight and preferably 1 to 4% by weight, based on the pre-emulsion A.

Emulsifier II

Adducts of, on average, 20 to 50 and preferably 20 to 30 moles of ethylene oxide with fatty alcohols containing 16 to 22 and preferably 16 to 18 carbon atoms may be used as emulsifier II. Typical examples are adducts of, on average, 25 to 30 moles of ethylene oxide with stearyl alcohol, isostearyl alcohol, oleyl alcohol, elaidyl alcohol, petroselinyl alcohol, linolyl alcohol, linolenyl alcohol, arachyl alcohol, gadoleyl alcohol, behenyl alcohol and erucyl alcohol and the technical mixtures thereof obtained, for example, in the high-pressure hydrogenation of native fatty acid methyl esters or aldehydes from Roelen's oxosynthesis. Adducts of, on average, 25 to 30 moles of ethylene oxide with technical cetostearyl alcohols are preferably used.

Other emulsifiers which may be used are adducts of, on average, 10 to 40 moles of ethylene oxide with sterols of vegetable and/or animal origin. By sterols are meant steroids containing 27 to 30 carbon atoms which only contain a hydroxy group at the C-3 and no other functional groups and which are often incorrectly termed stearins [ROEMPP Chemie Lexikon, Vol. 5, 1992, page 4302]. Typical examples are adducts of, on average, 10 to 40 moles and preferably 25 to 30 moles of ethylene oxide with zoosterols, such as for example cholesterol, lanosterol, spongosterol or stellasterol, or phytosterols, such as for example ergosterol, stigmasterol and sitosterol. Adducts of, on average, 25 to 30 moles of ethylene oxide with soya sterol are particularly preferred.

One preferred embodiment of the invention is characterized by the use of mixtures of adducts of, on average, 20 to 50 moles of ethylene oxide with fatty alcohols containing 16 to 22 carbon atoms and sterols of vegetable and/or animal origin. A typical example is a mixture of an adduct of, on average, 30 moles of ethylene oxide with cetostearyl alcohol and an adduct of, on average, 25 moles of ethylene oxide with soya sterol in a ratio by weight of 1:5 to 5:1 and preferably 2:1. The emulsifiers II may be used in quantities of 1 to 10% by weight and preferably 2.3 to 6.5% by weight, based on the multiple w/o/w emulsion.

In one particular embodiment of the invention, fatty alcohols containing 12 to 22 and preferably 16 to 18 carbon atoms may be added to emulsifier II as coemulsifiers, forming a liquid crystalline network in the emulsifier phase and contributing towards a further improvement in the stability of the resulting w/o/w emulsions. Suitable fatty alcohols are, for example, technical cetostearyl alcohols. The ratio by weight between emulsifier II and coemulsifier may be 1:1 to 1:2 and is preferably 1:1.5 to 1:1.8.

Production of Pre-Emulsion A

To produce the pre-emulsion, the oil is initially introduced into a stirred apparatus and the lipophilic emulsifier I is subsequently added. The components are homogenized with intensive shearing, i.e. at a stirrer speed of 1000 to 2000 r.p.m. and preferably 1200 to 1700 r.p.m. Centripetal turbines or, more particularly, colloid mills, for example, may be used as the stirred apparatus. It has proved to be of particular advantage to carry out the production of the pre-emulsion A at elevated temperature, i.e. at 50° to 90° C. and preferably at 70° to 80° C. The homogenization time is normally between 5 and 40 minutes and preferably between 10 and 30 minutes. In addition, it is advisable to add salt, preferably magnesium sulfate, to the pre-emulsion in quantities of 0.5 to 2% by weight, based on the pre-emulsion, for stabilization.

Accordingly, the composition of the pre-emulsion A is typically a1) 10 to 30 (preferably 15 to 25)% by weight of oil;

a2) 1 to 10 (preferably 1 to 4)% by weight of emulsifier I;

a3) 0.5 to 2 (preferably 0.5 to 1)% by weight of salt;

a4) ad 100% by weight water.

The water content of pre-emulsion A is typically between 58 and 88.5% by weight and preferably between 70 and 83% by weight.

Production of the Multiple w/o/w Emulsion

To produce the multiple w/o/w emulsion, pre-emulsion A is initially introduced into a stirred apparatus and the aqueous emulsifier II is subsequently added. The pre-emulsion A may be used in quantities of 50 to 90% by weight and preferably 65 to 80% by weight, based on the multiple w/o/w emulsion. The components are homogenized with gentle shearing, i.e. at a stirrer speed of 10 to 500 r.p.m. and preferably 150 to 250 r.p.m. Centripetal turbines or, more particularly, colloid mills may again be used as the stirred apparatus. It has proved to be of particular advantage to carry out the production of the multiple w/o/w emulsion at 20° to 60° C. and, more particularly, at 20° to 25° C. The homogenization time is typically between 5 and 50 mins. and preferably between 10 and 30 mins.

Accordingly, the composition of the multiple w/o/w emulsion is typically b1) 50 to 90 (preferably 65 to 80)% by weight of pre-emulsion b2) 1 to 10 (preferably 2 to 7)% by weight of emulsifier II b3) 0 to 5 (preferably 1 to 4)% by weight of coemulsifier b4) balance ad 100% by weight water The water content of the multiple w/o/w emulsion (including the water content of pre-emulsion A) is typically between 57 and 93% by weight and preferably between 74 and 89% by weight.

The present invention also relates to particularly storage-stable multiple w/o/w emulsions containing 15 to 20% by weight of dioctyl cyclohexane 1 to 5% by weight of triglycerol diisostearate/glycerol monooleate (4:1 parts by weight)

0.5 to 2% by weight of magnesium sulfate 1 to 3% by weight of cetostearyl alcohol 30 EO adduct 0.5 to 2% by weight of sterol 25 EO adduct 1 to 4% by weight of cetostearyl alcohol ad 100% by weight water.

Commercial Applications

The multiple w/o/w emulsions obtainable by the process according to the invention are stable, even in the event of prolonged storage, and readily biodegradable. They are suitable for accommodating active substances which would otherwise be immiscible with one another and for the controlled delayed release thereof.

Accordingly, the present invention also relates to the use of the multiple w/o/w emulsions obtainable by the process according to the invention for the production of cosmetic and pharmaceutical products, more particularly formulations for the cleaning and care of the hair and body, in which the multiple emulsions may be present in quantities of 1 to 99% by weight and preferably 10 to 50% by weight, based on the particular product.

The following Examples are intended to illustrate the invention without limiting it in any way.

EXAMPLES

I Substances Used
a) Oils
a1) Cetiol® S, a product of Henkel KGaA, Düsseldorf, FRG Dioctyl cyclohexane
a2) Cetiol® OE, a product of Henkel KGaA. Düsseldorf, FRG Dioctyl-n-octyl ether
b) Emulsifier I
b1) Dehymuls® B, Sidobre-Sinnova, Meaux, France Polyglycerol diisostearate, degree of condensation =5
b2) Monomuls® 90-O-18, Chemische Fabrik Grünau, Illertissen, FRG Glycerol monooleate, monoglyceride content 90% by weight
c) Emulsifier II
c1) Mergital® E 1471, Sidobre-Sinnova, Meaux, France Cetostearyl alcohol 30 EO adduct
c2) Generol® 122 E 25, Henkel KGaA, Düsseldorf, FRG Soya sterol 25 EO adduct Production Example 1
1a) Pre-emulsion A:
20 g of Cetiol® S and 4 g of Dehymuls® B were introduced into a centripetal turbine, after which a solution of 0.7 g of magnesium sulfate in 75 ml of water was added. The reaction mixture was then homogenized for 10 minutes at 80° C. at a speed of 1500 r.p.m. The speed was then reduced first to 1125 r.p.m. and then to 750 r.p.m., the reaction mixture being homogenized for another 10 minutes at those speeds.

1b) Multiple w/o/w emulsion:
77 g of pre-emulsion A were initially introduced, a solution of 2.1 g of Mergital® E 1471 and 1 g of Generol® 122 E 25 in 20 g of water was added over a period of 40 s and the whole was homogenized for 30 minutes at ambient temperature at a speed of 200 r.p.m.

Production Example 2
2a) Pre-emulsion A:
20 g of Cetiol® OE and 4 g of Monomuls® 90-O-18 were introduced into a centripetal turbine, after which a solution of 0.7 g of magnesium sulfate in 75 ml of water was added. The reaction mixture was then homogenized for 10 minutes at 80° C. at a speed of 1500 r.p.m. The speed was then reduced first to 1125 r.p.m. and then to 750 r.p.m., the reaction mixture being homogenized for another 10 minutes at those speeds.

2b) Multiple w/o/w emulsion:
77 g of pre-emulsion A were initially introduced, a solution of 2.1 g of Mergital® E 1471 and 1 g of Generol® 122 E 25 in 20 g of water was added over a period of 40 s and the whole was homogenized for 30 minutes at ambient temperature at a speed of 200 r.p.m.

Production Example 3:
3a) Pre-emulsion A:
20 g of Cetiol® S and 4 g of Dehymuls® B were introduced into a centripetal turbine, after which a solution of 0.7 g of magnesium sulfate in 75 ml of water was added. The reaction mixture was then homogenized for 10 minutes at 80° C. at a speed of 1500 r.p.m. The speed was then reduced first to 1125 r.p.m. and then to 750 r.p.m., the reaction mixture being homogenized for another 10 minutes at those speeds.

3b) Multiple w/o/w emulsion:
60 g of pre-emulsion A were initially introduced, a solution of 1.4 g of Mergital® E 1471, 0.7 g of Generol® 122 E 25 and 3.52 g of cetostearyl alcohol in 34.4 g of water was added over a period of 40 s and the whole was homogenized for 30 minutes at 60° C. at a speed of 200 r.p.m.

What is claimed is:

1. A process for the production of a multiple w/o/w emulsion comprising the steps of: (1) forming a w/o pre-emulsion by mixing together an aqueous emulsifier and a mixture comprised of an oil and a lipophilic emulsifier wherein said pre-emulsion is comprised of: (a) from about 10 to about 30% by weight of an oil selected from the group consisting of a dialkyl cyclohexane and a dialkyl ether and, (b) from about 1 to about 10% by weight of an emulsifier consisting of a lipophilic emulsifier selected from the group consisting of a glycerol fatty acid ester, an oligoglycerol fatty acid ester, a polyglycerol fatty acid ester, and combinations thereof; (2) mixing said pre-emulsion with from about 1 to about 10% by weight of the multiple w/o/w emulsion of an emulsifier, in aqueous form, consisting of an emulsifier selected from the group consisting of a fatty alcohol, an adduct of ethylene oxide with a fatty alcohol, an adduct of ethylene oxide with a sterol and combinations thereof; wherein the amount of said pre-emulsion is from about 50 to about 90% by weight of said multiple w/o/w emulsion and wherein the shearing force employed to mix the components of said pre-emulsion is greater than the shearing force employed to mix said pre-emulsion and said aqueous emulsifier.

2. The process of claim 1 where said lipophilic emulsifier is a monoester or a diester of glycerol with $C_{12-22}$ fatty acid.

3. The process of claim 1 where said lipophilic emulsifier is a monoester or a diester of an oligoglycerol or a monoester or a diester of a polyglycerol mixture having a degree of glycerol self-condensation of from 2 to 10 with a $C_{12-22}$ fatty acid.

4. The process of claim 1 where said emulsifier in step (2) is a mixture comprised of adducts of, on average, 20 to 50 moles of ethylene oxide with a $C_{16-22}$ fatty alcohol.

5. The process of claim 1 where said emulsifier in step (2) is a mixture comprised of adducts of, on average, 10 to 40 moles of ethylene oxide with a sterol of vegetable and/or animal origin.

6. The process of claim 1 where said emulsifier in step (2) is a mixture comprised of $C_{12-22}$ fatty alcohols.

7. The process of claim 1 wherein in step (1) from about 15 to about 25% by weight of oil is present in the pre-emulsion.

8. The process of claim 1 wherein in step (1)(a) the oil is a dialkyl cyclohexane of the formula $R^1$—C—$R^2$ wherein $R^1$ and $R^2$ are independently alkyl radicals containing from 1 to 12 carbon atoms and C is a cyclohexyl radical.

9. The process of claim 1 wherein in step (1)(a) the oil is a dialkyl ether of the formula $R^3$—O—$R^4$ wherein $R^3$ and $R^4$ are independently alkyl radicals containing 6 to 22 carbon atoms.

10. The process of claim 1 wherein in step (1)(b) from about 1 to about 4% by weight of lipophilic emulsifier is present.

11. The process of claim 1 wherein in step (1) from about 0.5 to about 2% by weight, based on the pre-emulsion, of a salt is added to stabilize the pre-emulsion.

12. The process of claim 11 wherein the salt is magnesium sulfate.

13. The process of claim 1 wherein step (1) is carried out at a temperature in the range of from about 50° to about 90° C.

14. The process of claim 13 wherein said temperature is in the range of from about 70° to about 80° C.

15. The process of claim 15 wherein step (2) is carried out at a temperature in the range of from about 20° to about 600° C.

16. The process of claim 15 wherein said temperature is in the range of from about 20° to about 25° C.

17. The process of claim 1 wherein the water content of the multiple w/o/w emulsion is from about 57 to about 93% by weight.

18. The process of claim 17 wherein said water content is from about 74 to about 89% by weight.

* * * * *